US006729328B2

(12) United States Patent
Goldemann

(10) Patent No.: US 6,729,328 B2
(45) Date of Patent: May 4, 2004

(54) BREATHING-CONTROLLED INHALATION DEVICE FOR DRY POWDER AND METHOD FOR THE EVEN DISTRIBUTION OF THE DRY POWDER IN THE AIR

(75) Inventor: Raul Goldemann, Modlin (IL)

(73) Assignees: Raul Goldenmann (IL); Ofer Frydling (DE); Angela Eckardt (DE)

( * ) Notice: Subject to any disclaimer, the term of this patent is extended or adjusted under 35 U.S.C. 154(b) by 0 days.

(21) Appl. No.: 10/117,762

(22) Filed: Apr. 4, 2002

(65) Prior Publication Data

US 2002/0129817 A1 Sep. 19, 2002

Related U.S. Application Data

(63) Continuation of application No. PCT/DE00/03527, filed on Oct. 6, 2000.

(30) Foreign Application Priority Data

Oct. 6, 1999 (DE) ........................................ 199 48 289
Jun. 6, 2000 (DE) ........................................ 100 27 631

(51) Int. Cl.[7] .............................................. A61M 15/08
(52) U.S. Cl. ............................ 128/203.15; 128/203.12; 128/200.18; 128/203.18
(58) Field of Search ....................... 128/203.15, 203.18, 128/203.12, 200.14, 200.18, 200.22; 239/370

(56) References Cited

U.S. PATENT DOCUMENTS 5,320,714 A * 6/1994 Brendel ................. 128/203.15
5,437,270 A * 8/1995 Braithwaite ............ 128/203.15
5,483,954 A * 1/1996 Mecikalski ............ 128/203.15
5,505,196 A 4/1996 Herold et al. .......... 128/203.15
5,533,505 A * 7/1996 Kallstrand et al. ..... 128/203.15
5,699,789 A 12/1997 Hendricks .............. 128/203.15
5,857,457 A * 1/1999 Hyppola ................ 128/203.15
6,065,472 A * 5/2000 Anderson et al. ...... 128/203.21
6,332,461 B1 * 12/2001 Hyppola ................ 128/203.15

FOREIGN PATENT DOCUMENTS

| | | |
|---|---|---|
| DE | 4340768 | 6/1995 |
| EP | 0938907 | 9/1999 |
| WO | 9834661 | 8/1998 |
| WO | 9933505 | 7/1999 |

* cited by examiner

*Primary Examiner*—Weilun Lo
*Assistant Examiner*—Darwin P. Erezo
(74) *Attorney, Agent, or Firm*—Baker Botts LLP

(57) ABSTRACT

A breathing-controlled inhalation device for dry powder comprises a casing with a mouthpiece, a reservoir for dry powder in the casing, and an air guiding unit between a transfer area for the dry powder and the mouthpiece. A dosing conveyor accepts a predetermined amount of powder from the conveyor and upon manual depression of the conveyor, transfers the powder to the inlet of the air guiding unit. The air guiding unit has an air flow channel comprising a cylindrical component having semispherical indentations formed alternatively from opposite walls and extending into the channel to increase turbulence in the air flow and enhance distribution of the particles.

7 Claims, 5 Drawing Sheets

B - B

BREATHING-CONTROLLED INHALATION DEVICE FOR DRY POWDER AND METHOD FOR THE EVEN DISTRIBUTION OF THE DRY POWDER IN THE AIR

This application is a Continuation of International Application PCT/DE00/03527, filed Oct. 6, 2000.

FIELD OF THE INVENTION

The invention relates to a breathing-controlled inhalation device for dry powder, particularly dry powder which has been mixed with medicines.

BACKGROUND OF THE INVENTION

For a long time, one of the primary methods for the treatment of respiratory diseases has been the introduction of suitable agents into the respiratory tract. In this regard, the devices used for this—often also as mechanisms to stimulate transport—have gained an ever-growing significance because of the increase in the number of respiratory diseases in the last number of years. In particular, breathing-controlled devices, which offer a mild alternative to propellant-controlled devices, are being increasingly used, since they do not have the unpleasant effect of stimulating colds.

A device of this type is known from DE 40 04 904 A1, in which the agent is kept ready on the periphery of a dosing drum and is regulated radially. The inside of the dosing drum contains a control unit for the active output of the divided inhalation amount from open dosing recesses in a radially outwards direction. Moreover, the bottom of the equally-angled distributed arranged dosing recesses forming slides are centrally cam-controlled. Since this control mechanism is additionally activated by a control key which lies practically along the whole length of the device, the expenditure in this regard is considerable. Moreover, the dosed medicines can be added by means of a forced emptying of the dosing recess. This can lead to a dangerous over-dosage. In terms of volume, the space which remains for the reservoir represents only a fraction of the pocket-format device.

DE 198 25 434 A1 describes an inhalation device in which the dosing device is made taut before the intake of the medicine and is held in this condition on a stopper which can be moved during inhalation. The dosing device is released and accelerated during inhalation, so that the accelerated movement is abruptly interrupted in that the stopper on the dosing device strikes the casing or the bottom of the casing. This sudden interruption of the rotation of the dosing device results in the powdery medicine being released from the dosing cavity at greater speed and being widely distributed in the air channel. This design is also relatively complicated and, in addition, demonstrates the lack of inclusion of flow-orientated air guidance. The air channel has a straight design and does not permit any circulation or turbulence of the agents to be inhaled.

DE 43 40 768 A1 describes a device for the inhalation of powdery agents, which is provided with a special turbulence chamber in spiral form, the complicated construction design of which case disadvantageous. Although, the turbulence chamber does facilitate a certain evenness in the distribution of the powder, the spiral turning of the turbulence chamber leads increasingly to friction and resistance points which prevent complete passage of the particles.

Furthermore, in U.S. Pat. No. 5,699,789, an inhaler for dry powder, in which a dosing conveyor is provided, has a reservoir container projecting into the air-flow channel which takes a predetermined amount of dry powder and is positioned inside the air guiding unit. The air which passes through the air-flow channel has to move around both the reservoir container and a nose located near the inlet opening. In this way, a certain turbulence of the air is achieved, though it cannot be ensured that all the conducted dry powder is conveyed through the inlet opening in a homogenously distributed manner.

In EP-A-938907 an inhalation device for dry powder is described in which inwardly projecting plates are provided alternately in the air-flow channel in order to achieve a turbulence of the air. Because of the high volume of clearance areas in this device it cannot be ensured that the total amount of dosed powder is conveyed outwards during inhalation.

A similar inhalation device is shown in the WO-A-993305. Powder residue can also remain in the device in this case, which adulterates the dosage.

SUMMARY OF THE INVENTION

The invention therefore relates to the creation of a breathing-controlled inhalation device of the type mentioned at the beginning, which, as a result of a simple design with few simple components, can be cost-effectively manufactured, has a small size, is provided with a double dose protector, and with which a complete and even distribution of the dry powder during the inhalation procedure can be attained. Furthermore, a method is provided which enables a complete and even respirable distribution in the breath of the dry powder to be inhaled.

The invention overcomes the disadvantageous of prior art devices with an air guiding unit consisting of an essentially cylindrical central component which is provided alternately with semi-spherical indentations reaching from opposite walls of the central component into the air-flow channel, the air-flow channel having a rising inhalation area in the application area of the inhalation device, and with a dosing conveyor positioned directly downwards in front of the inhalation area. An air guiding unit designed in this manner permits a very effective and complete distribution of the dry powder during the inhalation procedure, since the air which has been drawn in circulates and the rising particles can be mixed with each other in an optimal way.

By means of this special arrangement of the inhalation area, the dry powder can, when required, get directly into the air-flow channel and can from there be directly drawn in. In this way, the risk of the intrusion of moisture or of an unintentional proportional loss of portioning during inhalation is reduced.

In a preferred embodiment of the invention the casing is provided with an air inlet which is positioned downwards opposite the inhalation area. The opening of the device in the form of the air inlet permits an increased intake of the particles, independent of the remaining air.

Moreover, the inhalation device of the invention comprises a dosing conveyor in the form of a flat slide number having a laterally oriented dosing bole hole for receiving a predetermined amount of dry powder from the reservoir. The slide member is movable between a first position in which it receives the dry powder and a dosing position in which the borel hole is directly in front of the inhalation area of the air guiding unit. In the dosing position, the slide keeps the reservoir essentially locked.

In this way double dose protection can be ensured, since only the amount of dry powder located in the dosing drill hole is available for each inhalation procedure. Should the inhalation procedure be broken off or interrupted, the remainder of the dry powder located in the dosing drill hole is conveyed back into the reservoir or is removed from the inhalation area and is thereby not available for a further inhalation procedure.

A favourable design feature here ensures that the slide is held in a spring-loaded start position in which the reservoir is locked and that the slide is moveable against a spring resistance into the dosing position. A spring-controlled movement mechanism guarantees that accidental escape, unintended intrusion of moisture or an unintentional actuation of the device are practically excluded. Moreover, an important advantage of this design is that, because of the simplicity of the functional construction, besides the necessary readjusting spring, only one moving part (dosing conveyor) is required, which further guarantees the constant availability for use of the device and minimizes the risk of any possible errors.

The air guiding unit can have a single-part or multi-part design, whereby glass or plastic as cost-effective materials have proved themselves to be particularly suitable. Other suitable materials, such as metals, may also of course be used for the manufacture of the air guiding unit.

Furthermore, the advantages of the invention are achieved in that the acceleration of the air-flow is effected by means of cross section narrowings in the air guiding unit in the form of semi-spherical indentations which project alternately into the airflow channel in the air guiding unit from opposite walls of the central component. The air circulation and flow guiding provided in this special method make possible effective turbulence of the individual dry powder particles. The movements of the air spread the particles evenly and guarantee optimum distribution at the moment of inhalation.

By means of the concentration of the flow of particles with kinetic energy their movement and distribution capacity is increased and a possible loss of energy caused by gravity is compensated, which makes for an overall improvement of the turbulence effect.

BRIEF DESCRIPTION OF THE INVENTION

The invention will be explained in greater detail in the following detailed description thereof, taken in conjunction with the appended drawings in which:

FIG. 1a is a front view of an inhalation device according to the invention in non-operational mode with open mouthpiece;

FIG. 1b is a sectional view along the line A—A of FIG. 1a;

FIG. 1c is a sectional view along the line B—B of FIG. 1b;

FIG. 1d is a perspective representation of the inhalation device according to FIGS. 1a–1c;

FIG. 2a is a front view of an inhalation device according to the invention, in non-operational mode with closed mouthpiece;

FIG. 2b is a sectional view along the line A—A of FIG. 2a;

FIG. 2c is a sectional view along the line B—B of FIG. 2b;

FIG. 2d is a perspective representation of the inhalation device according to FIGS. 2a–2c;

FIG. 3a is a front view of an inhalation device according to the invention in halation operative mode with open mouthpiece;

FIG. 3b is a sectional view along the line A—A of FIG. 3a;

FIG. 3c is a sectional view along the line B—B of FIG. 3b;

FIG. 3d is a perspective representation of the inhalation device according to FIGS. 3a–3c;

FIG. 4a is a front view of an inhalation device according to the invention in inhalation operative mode with closed mouthpiece;

FIG. 4b is a sectional view along the line A—A of FIG. 4a;

FIG. 4c is a sectional view along the line B—B of FIG. 4b;

FIG. 4d is a perspective representation of the inhalation device according to FIGS. 4a–4c.

DETAILED DESCRIPTION OF THE INVENTION

Figure 4:
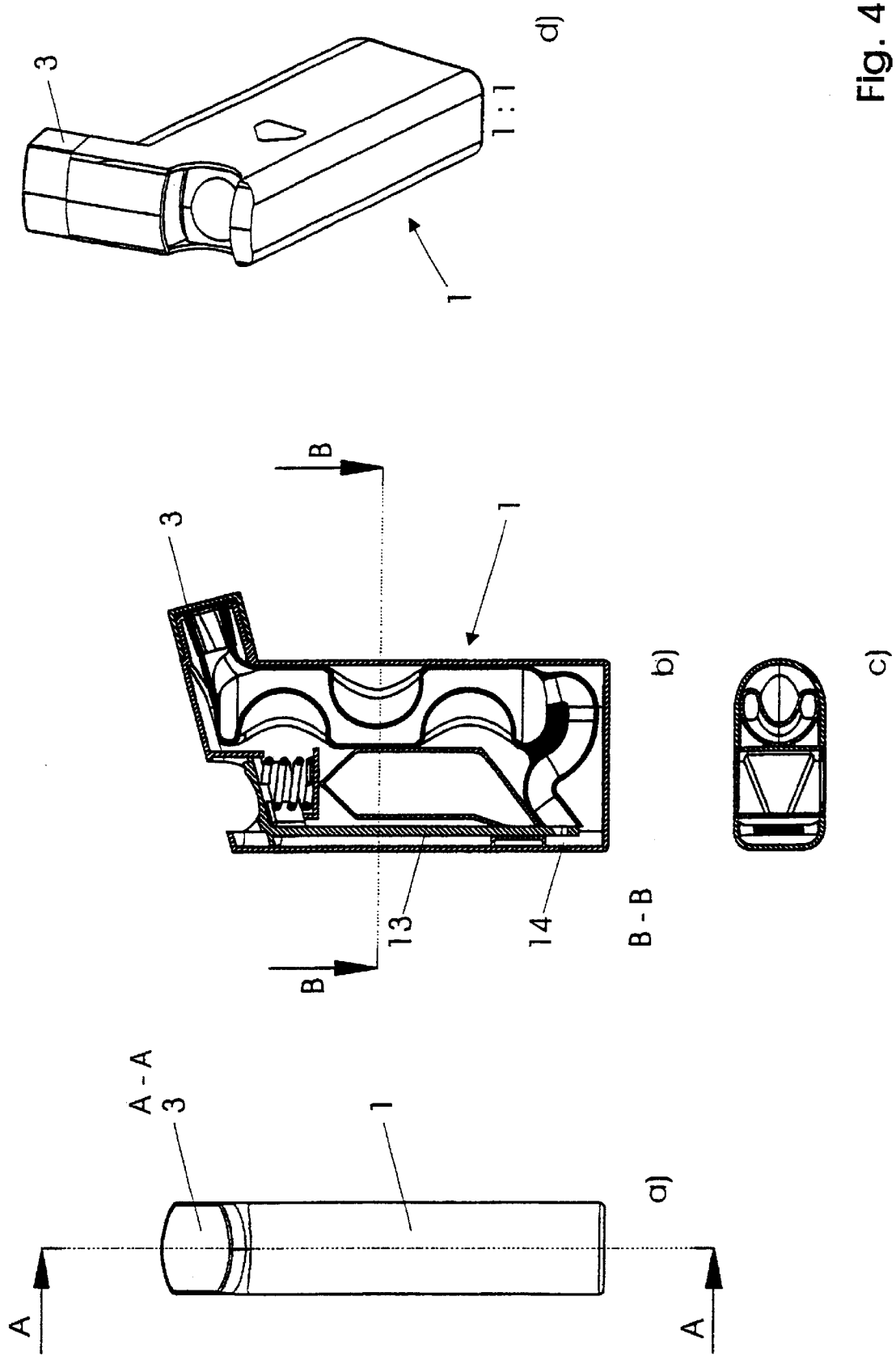
Figure 5:
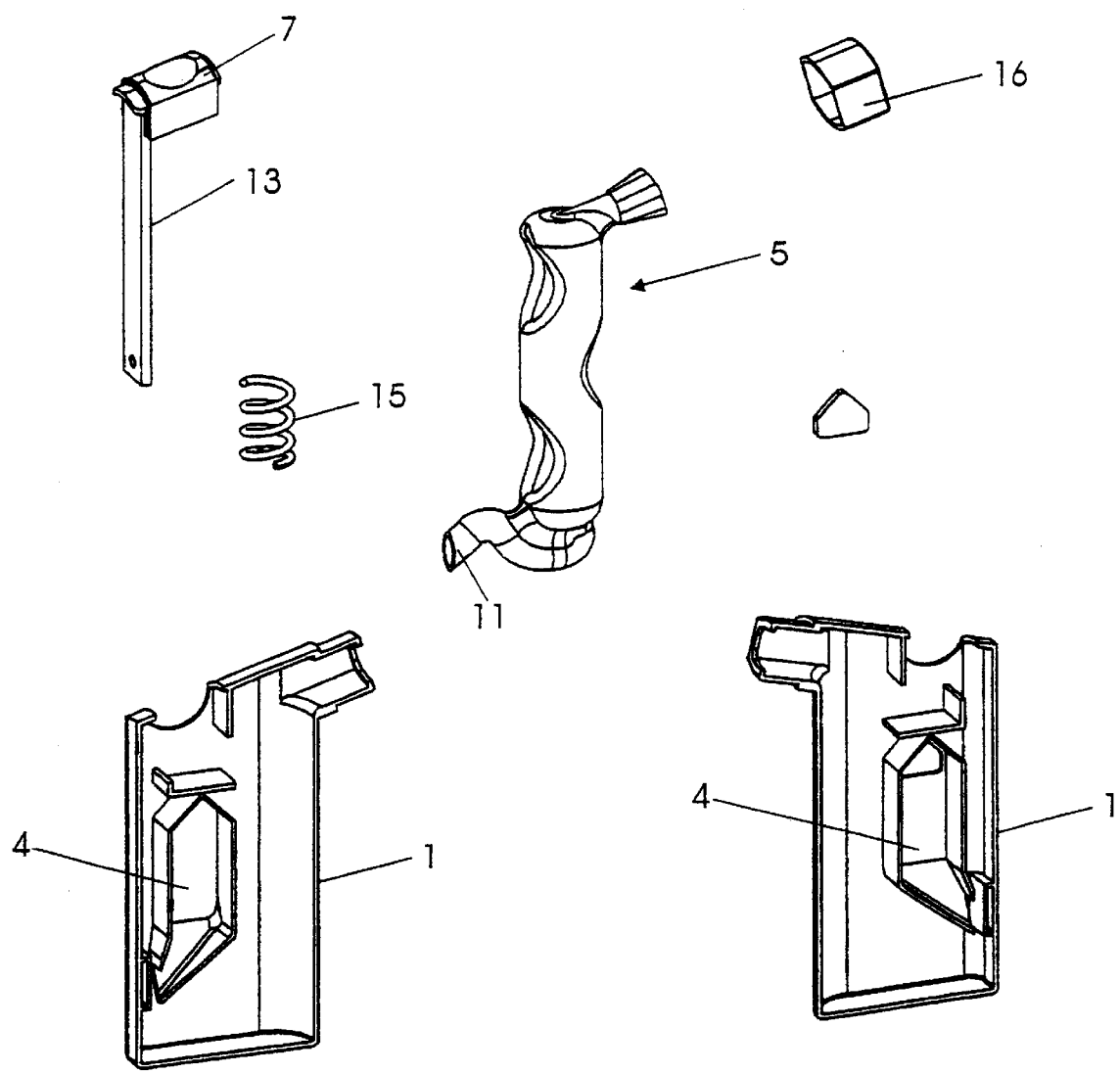
FIG. 5 is an exploded view showing the individual components of the breathing-controlled inhalation device according to the invention.

As shown in FIGS. 1a–d, 2a–d, 3a–d, and 4a–d, the dry powder reservoir 4 is essentially kept locked on a permanent basis both in non-operational and operational mode by means of a dosing conveyor 7 (shown separately in FIG. 5) designed as a slide 13 (also shown separately in FIG. 5). With regard to the dry powder located in the reservoir an intrusion of external moisture or impurities can thereby be almost ruled out.

The dosing conveyor 7 has a laterally positioned dosing bore hole 14 for the intake of the dry powder. Before the beginning of the inhalation procedure the dosing drill hole 14 is located to be in communication with the reservoir 4. A cap 16 (shown separately in FIG. 5) provides hygienic protection for the mouthpiece 3. After the cap 16 has been removed (FIGS. 1a and b) the inhalation device 1 is held perpendicularly to the mouthpiece 3, upwards and away from the mouth. After the user has first of all breathed deeply out, avoiding contact with the mouthpiece—i.e. without blowing into the mouthpiece 3—he then covers the mouthpiece 3 with the lips. To start the inhalation procedure and to transfer the dosing conveyor 7 into the dosing position, the conveyor 7 is manually pressed down against the force of spring 15 (shown separately in FIG. 5), as illustrated in (FIGS. 3b and 3d, as well as in FIGS. 4b and 4d.

Figure 1:
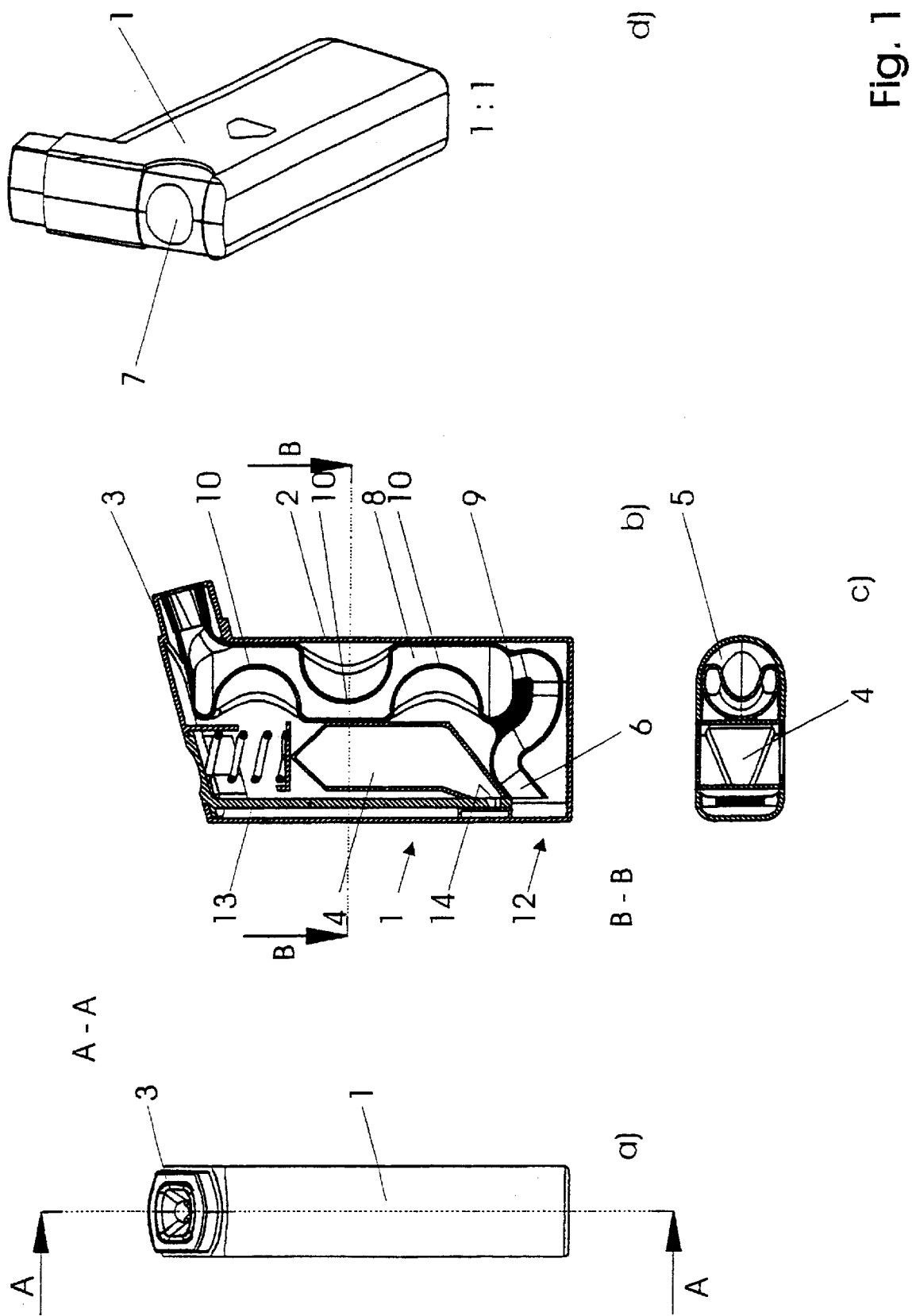
Figure 2:
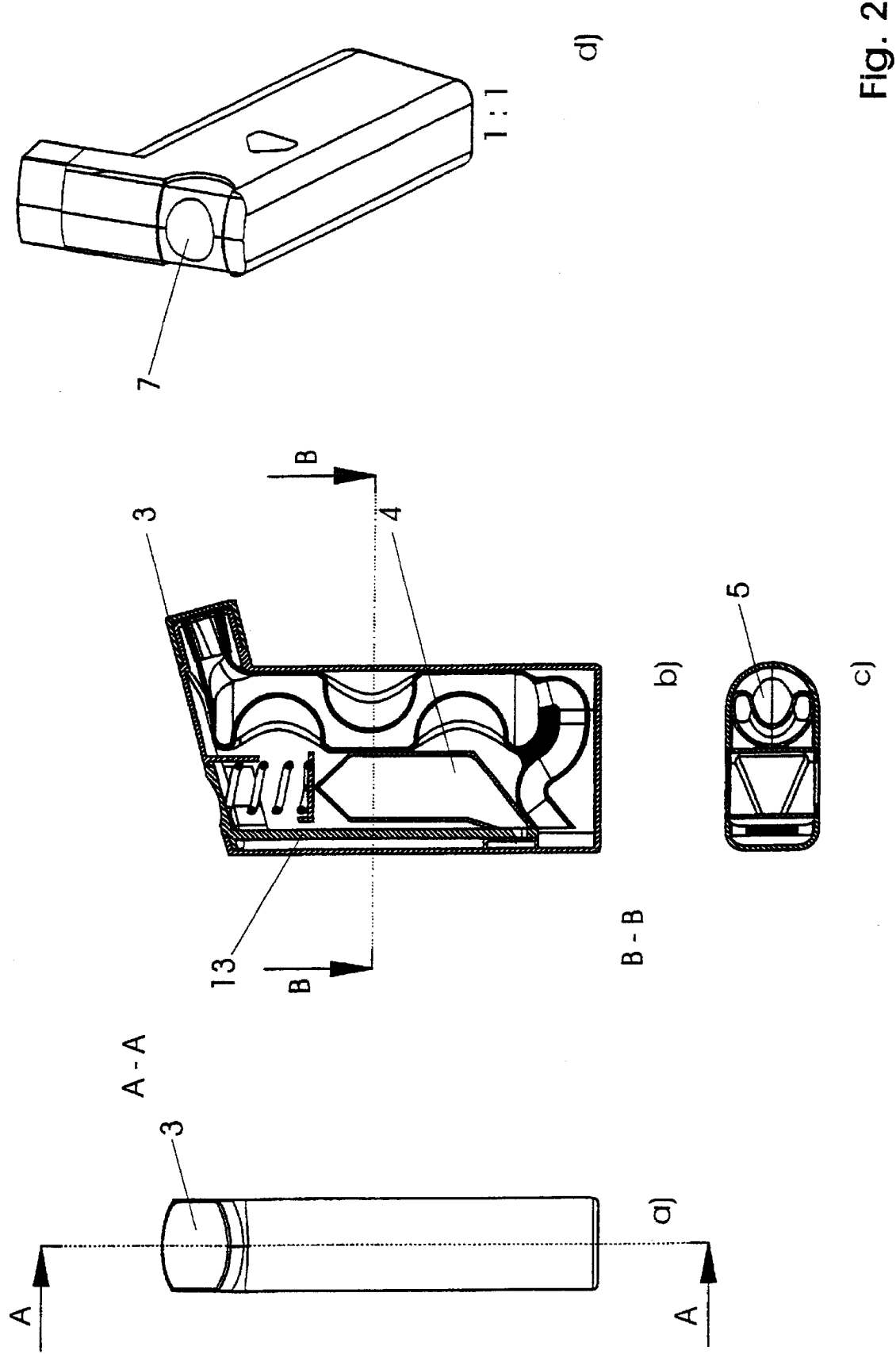
Figure 3:
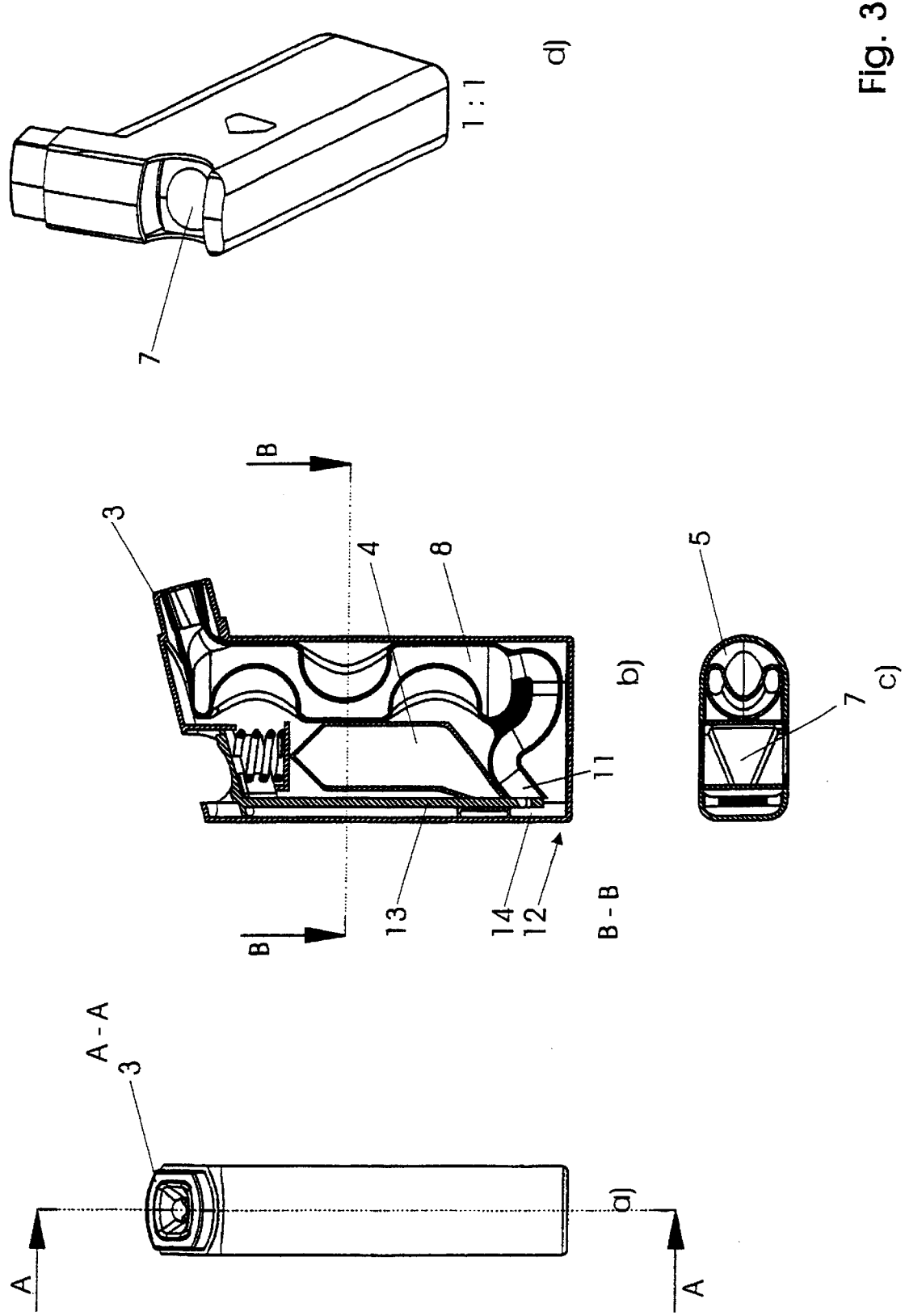

The dosing drill hole 14 is now located directly in front of the inhalation area 11 of the air guiding unit 5 (FIGS. 3b and 4b). Reservoir 4 communicates with the dosing conveyor 7 such that the predetermined amount of dry powder fills the dosing hole 14 and when conveyor 7 is depressed, hole 14 is positioned directly at the inhalation area 11 of the air guiding unit 5. Thus, it is ensured that no unintended loss of dosage occurs before or during inhalation occurs.

The user now breathes in as deeply as possible through the mouth. By means of an air inlet 12 located in casing 2 opposite the inhalation area 11, air is drawn in and an air-flow is created inside the inhalation device 1. This carries the particles of the dry powder via the dosing drill hole 14 through the transfer and inhalation area 6, 11 and finally through the air guiding unit 5 until an escape of the particles through the mouthpiece 3 directly into the user's respiratory tract takes place.

Should the inhalation procedure be broken off or interrupted before completion and downward pressure on conveyor 7 released, the remainder of the dry powder located in the dosing drill hole 14 is conveyed back into the reservoir 4, since the spring returns the dosing conveyor to the start position, or at least removed from the inhalation area and the powder is thereby no longer available for a further inhalation procedure. In this way, the danger of a double dosage is avoided.

The air drawn to the device by inhalation is conducted through an air guiding unit 5 (shown separately in FIG. 5) in such a way that an alternate acceleration and subsequent deceleration of the air-flow takes place because of simultaneous turbulence and change in the direction of the flow.

The air guiding unit 5 comprises an essentially cylindrical central component 9 provided alternately with semispherical indentations 10 which reach from opposite walls of the central component 9 into the air-flow channel 8 (FIG. 1*b*).

The air guiding unit 5 can have a single-part or multi-part design, whereby glass or plastic as cost-effective materials have proved themselves to be particularly suitable. Other suitable materials, such as metals, may also of course be used for the manufacture of the air guiding unit.

The acceleration of the air-flow is thereby effected by means of cross section narrowings in the air guiding unit 5, which are alternately located on opposite sides in the air guiding unit 5. The air guiding unit 5, designed in this manner, permits a very effective and complete distribution of the dry powder during the inhalation procedure, since the air which has been drawn in circulates and the rising particles can be mixed with each other in an optimal way.

By means of the concentration of the flow of particles with kinetic energy their movement and distribution capacity is increased and a possible loss of energy caused by gravity is compensated, which makes for an overall improvement of the turbulence effect.

What is claimed is:

1. A breathing-controlled inhalation device for dry powder medication comprising:

a casing having a mouthpiece;

a reservoir for dry powder medication within said casing;

an air flow channel in said casing having an outlet coupled to said mouthpiece, an inlet and a transfer area, said channel comprising a generally cylindrical component having semispherical indentations formed alternately on opposite walls thereof and extending into said cylindrical component, said channel having a flow area which rises in the region immediately following said transfer area when said device is in the application position; and a dosing conveyor for delivering a predetermined amount of dry powder medication from said reservoir to said transfer area of said air flow channel.

2. The inhalation device of claim 1, wherein said reservoir has an outlet positioned above the inlet of said air flow channel and said dosing conveyor comprises a vertically movable slide member having a hole therein sized to receive a predetermined amount of dry powder medication, said slide member being sliceable between a first position at which said hole is opposite the outlet of said reservoir to receive said predetermined amount of dry powder medication and a second position at which said hole is opposite the inlet of said air flow channel to permit said predetermined amount of dry powder medication to be drawn into said at flow channel.

3. The inhalation device of claim 2, further comprising a spring normally urging said slide member to said first position, said slide member being manually movable against the spring resistance to said second position.

4. The inhalation device of claim 2 further comprising an air inlet in said casing opposite the inlet to said air flow channel.

5. The inhalation device of claim 2 wherein said slide member locks said reservoir against release of dry powder medication when in said second position and limits release of dry powder medication to the volume of said hole when in said first position.

6. The inhalation device of claim 1 wherein said indentations are integrally formed in the walls of said generally cylindrical component.

7. The inhalation device of claim 1 wherein said cylindrical component of said air flow channel is the flow area which rises in the region immediately following said transfer area and connects said transfer area to said mouthpiece.

* * * * *